(12) United States Patent
Bernard et al.

(10) Patent No.: US 8,785,397 B2
(45) Date of Patent: Jul. 22, 2014

(54) COSMETIC USE OF APOLIPOPROTEIN D TYPE PROTEINS

(75) Inventors: Dominique Bernard, Paris (FR); Isabelle Castiel, Nice (FR); Lucie Simonetti, Vincennes (FR)

(73) Assignee: L'Oreal, Paris (FR)

( * ) Notice: Subject to any disclaimer, the term of this patent is extended or adjusted under 35 U.S.C. 154(b) by 180 days.

(21) Appl. No.: 12/602,246

(22) PCT Filed: Jun. 20, 2008

(86) PCT No.: PCT/IB2008/052440
§ 371 (c)(1),
(2), (4) Date: Dec. 22, 2009

(87) PCT Pub. No.: WO2009/001260
PCT Pub. Date: Dec. 31, 2008

(65) Prior Publication Data
US 2010/0216707 A1    Aug. 26, 2010

Related U.S. Application Data

(60) Provisional application No. 60/952,262, filed on Jul. 27, 2007.

(30) Foreign Application Priority Data

Jun. 22, 2007    (FR) ..................................... 07 55976

(51) Int. Cl.
*A61K 38/16*        (2006.01)
*A61K 8/64*         (2006.01)
*G01N 33/68*        (2006.01)

(52) U.S. Cl.
USPC ........................... 514/21.2; 436/86; 514/44 R

(58) Field of Classification Search
USPC ......... 514/12, 44 R, 8, 21.2; 424/7.1; 436/86; 536/23.1; 435/86
See application file for complete search history.

(56) References Cited

FOREIGN PATENT DOCUMENTS

WO    WO 2005/079821 A1    9/2005

OTHER PUBLICATIONS

International Search Report for International Application No. PCT/IB2008/052440, issued Dec. 8, 2008.

*Primary Examiner* — Chih-Min Kam
(74) *Attorney, Agent, or Firm* — Oliff PLC

(57) ABSTRACT

The subject of the present invention is the use, in particular the cosmetic and/or therapeutic use, of the apolipoprotein D, of polypeptides derived from this protein or of analogues thereof, of a nucleic sequence encoding such a polypeptide or of an agent modulating the activity or of the expression of such a polypeptide, in particular for stimulating terminal epithelial differentiation.

The invention also relates to the use of the protein apolipoprotein D, of polypeptides derived from this protein or of analogues thereof, or of a nucleic sequence encoding such a polypeptide as a marker for evaluating the state of the epidermis.

2 Claims, No Drawings

ID

SEQUENCE LISTING

```
<160> NUMBER OF SEQ ID NOS: 2

<210> SEQ ID NO 1
<211> LENGTH: 869
<212> TYPE: DNA
<213> ORGANISM: Homo Sapiens

<400> SEQUENCE: 1
gctgattctg catctggaaa ctgccttcat cttgaaagaa aagctccagg tcccttctcc      60
agccacccag ccccaagatg gtgatgctgc tgctgctgct ttccgcactg gctggcctct     120
tcggtgcggc agagggacaa gcatttcatc ttgggaagtg ccccaatcct ccggtgcagg     180
agaattttga cgtgaataag tatctcggaa gatggtacga aattgagaag atcccaacaa     240
cctttgagaa tggacgctgc atccaggcca actactcact aatggaaaac ggaaagatca     300
aagtgttaaa ccaggagttg agagctgatg gaactgtgaa tcaaatcgaa ggtgaagcca     360
ccccagttaa cctcacagag cctgccaagc tggaagttaa gttttcctgg tttatgccat     420
```

-continued

```
cggcaccgta ctggatcctg gccaccgact atgagaacta tgccctcgtg tattcctgta    480
cctgcatcat ccaactttt cacgtggatt ttgcttggat cttggcaaga aaccctaatc     540
tccctccaga aacagtggac tctctaaaaa atatcctgac ttctaataac attgatgtca    600
agaaaatgac ggtcacagac caggtgaact gccccaagct ctcgtaacca ggttctacag    660
ggaggctgca cccactccat gttacttctg cttcgctttc ccctacccca cccccccc     720 ataaagacaa accaatcaac cacgacaaag gaagttgacc tgaacatgta accatgccct    780
accctgttac cttgctagct gcaaaataaa cttgttgctg acctgcaaaa aaaaaaaaa    840 aaaaaaaaa aaaaaaaaa aaaaaaaa                                         869
```

<210> SEQ ID NO 2
<211> LENGTH: 189
<212> TYPE: PRT
<213> ORGANISM: Homo Sapiens

<400> SEQUENCE: 2

```
Met Val Met Leu Leu Leu Leu Ser Ala Leu Ala Gly Leu Phe Gly
1               5                   10                  15

Ala Ala Glu Gly Gln Ala Phe His Leu Gly Lys Cys Pro Asn Pro Pro
            20                  25                  30

Val Gln Glu Asn Phe Asp Val Asn Lys Tyr Leu Gly Arg Trp Tyr Glu
        35                  40                  45

Ile Glu Lys Ile Pro Thr Thr Phe Glu Asn Gly Arg Cys Ile Gln Ala
    50                  55                  60

Asn Tyr Ser Leu Met Glu Asn Gly Lys Ile Lys Val Leu Asn Gln Glu
65                  70                  75                  80

Leu Arg Ala Asp Gly Thr Val Asn Gln Ile Glu Gly Glu Ala Thr Pro
                85                  90                  95

Val Asn Leu Thr Glu Pro Ala Lys Leu Glu Val Lys Phe Ser Trp Phe
            100                 105                 110

Met Pro Ser Ala Pro Tyr Trp Ile Leu Ala Thr Asp Tyr Glu Asn Tyr
        115                 120                 125

Ala Leu Val Tyr Ser Cys Thr Cys Ile Ile Gln Leu Phe His Val Asp
    130                 135                 140

Phe Ala Trp Ile Leu Ala Arg Asn Pro Asn Leu Pro Pro Glu Thr Val
145                 150                 155                 160

Asp Ser Leu Lys Asn Ile Leu Thr Ser Asn Asn Ile Asp Val Lys Lys
                165                 170                 175

Met Thr Val Thr Asp Gln Val Asn Cys Pro Lys Leu Ser
            180                 185
```

COSMETIC USE OF APOLIPOPROTEIN D TYPE PROTEINS

This nonprovisional application is a national stage application of PCT/IB2008/052440, filed Jun. 20, 2008, which claims the benefit of U.S. Provisional Application No. 60/952,262, filed Jul. 27, 2007.

The subject of the present invention is the use, in particular the cosmetic and/or therapeutic use, of the protein apolipoprotein D, of polypeptides derived from this protein or of analogues thereof, of a nucleic sequence encoding such a polypeptide or of an agent modulating the activity or of the expression of such a polypeptide, in particular for stimulating terminal epithelial differentiation.

The invention also relates to the use of the protein apolipoprotein D, of polypeptides derived from this protein or of analogues thereof, or of a nucleic sequence encoding such a polypeptide as a marker for evaluating the state of the epidermis.

The epithelia are tissues whose cells are contiguous and integrally connected to each other and rest on a basal membrane. They form either an outer covering, for example at the surface of the skin, that is to say the epidermis, or an inner covering, at the surface of a mucous membrane. They can also form glands.

More precisely, these epithelia are structures whose homeostasis results from the use of a finely regulated set of intracellular and extracellular signals acting at all stages of cell proliferation, migration or differentiation, and of the synthesis of the various components of the extracellular matrix. These signals may result in particular from the action of factors produced by keratinocytes.

Maintaining the good physiological functions of an epithelium involves in particular terminal epithelial differentiation and/or the synthesis of proteoglycans.

As regards more particularly the epidermis, it is an epithelium which is conventionally divided into a basal layer of keratinocytes containing, in particular, skin stem cells and constituting the germinative layer of the epidermis, a so-called prickle cell layer consisting of several layers of polyhedral cells arranged on the basal layer, a so-called granular layer comprising one to three so-called layers of flattened cells containing distinct cytoplasmic inclusions, the keratohyalin granules, and finally a set of top layers, called horny layer (or *stratum corneum*) constituted of keratinocytes at the final stage of their differentiation, called corneocytes.

The stratum corneum, the outermost part of the skin which provides the barrier function between the body and the environment, and the hair shaft, the emerging part of the hair follicle which constitutes the hair, both represent the result of the process of differentiation of the keratinocytes. Epidermal differentiation follows a maturation process in which the keratinocytes of the basal layer differentiate and migrate, resulting in the formation of the corneocytes, completely keratinized dead cells. This differentiation is the result of perfectly coordinated phenomena which will lead to a constant thickness being maintained and which will thus bring about the homeostasis of the epidermis.

Numerous skin disorders or pathologies can result from a dysfunction in the homeostasis of the epidermis, and in particular a dysfunction in the terminal epithelial differentiation of the keratinocytes and/or in the synthesis of proteoglycans.

Accordingly, the main modifications concerning the epidermis are a reduction in the differentiation of the keratinocytes causing a deficiency in the protein matrix of the horny cell, an increase in metalloproteases, proteases degrading the extracellular matrix and which participate in skin ageing, and in a reduction in the synthesis of various glycosaminoglycans.

For example, in the case of aged skin, this dysfunction generally manifests itself by the appearance of wrinkles (microrelief and deep wrinkles), a loss of elasticity, by a rough feel and by dryness. From the histological point of view, flattening of the dermo-epidermal junction and a reduction in the thickness of the dermis and of the epidermis are observed. The content of collagen and of glycosaminoglycans decreases. The barrier function of the skin is impaired. All of these phenomena are exacerbated by chronic solar exposure.

Likewise, during menopause, the skin undergoes changes in all its compartments, namely epidermal and dermal compartments. The principal changes relating to the dermis are a reduction in the amount of collagen and in the dermal thickness. This causes, in menopausal women, a reduction in the thickness of the skin and/or of the mucous membranes. The women then feel a sensation of "dry skin" or of tight skin and an accentuation of the surface fine wrinkles and fine lines is observed. The skin exhibits a rough appearance to the touch. Finally, the skin exhibits a reduced softness.

It is already known that during the various stages of differentiation of the keratinocytes, several families of proteins come into play which each have a specific function. Among these, proteases play a vital role in desquamation, that is to say in the elimination of the corneocytes at the surface of the epidermis, and transglutaminases participate in the cross-linking of the proteins which will form the horny envelope of the skin.

The present invention results particularly from the characterization by the inventors, of the expression of apolipoprotein D, also called ApoD, in the horny layer of the human epidermis.

ApoD is a 29 KDa glycoprotein present, in humans, in the serum associated with the HDLs, and whose function is not yet clear. Its three-dimensional structure and its membership of the lipocalin family suggests that ApoD would be a transporter of small hydrophobic molecules and it would bind in particular bilirubin, cholesterol, progesterone, pregnenolone and arachidonic acid.

Large increases of this protein are observed in several diseases in humans. Thus, ApoD is highly accumulated in the cystic fluid of the mammary gland of women affected by the disease: "Gross Cystic Fluid Disease", a form of benign cancer of the mammary gland.

Moreover, ApoD is overexpressed during the regeneration of the nerves. Indeed, following a lesion of the peripheral nerve, large increases in messenger RNA and in the protein are observed, which suggests that ApoD might play an important role in the maintenance of the peripheral nervous system.

Finally, and more recently, it has been found that ApoD accumulates in the cerebrospinal fluid and in the hippocampus of subjects suffering from Alzheimer's disease. A more exhaustive analysis has demonstrated large increases in several other human neurodegenerative diseases such as meningoencephalitis, cardiovascular accident, motoneuron disease and dementia. This suggests that ApoD might also play an important role in the maintenance of the central nervous system.

On the other hand, to the knowledge of the inventors, apolipoprotein D had up until now not been identified as being a protein of the human stratum corneum.

Indeed, contrary to all expectations, apolipoprotein D has also turned out to be a potential marker of the physiological state of the skin, in particular in terms of ageing. Thus, as is evident from the tests presented below, the inventors have observed, unexpectedly, on the one hand, the expression of this glycoprotein in the *stratum corneum*, and, on the other hand, a significant decrease in its expression during ageing of the epidermis.

Consequently, according to one of its first aspects, the subject of the present invention is a cosmetic or non-therapeutic use of an effective quantity of at least one polypeptide derived from apolipoprotein D and, in particular, having an amino acid sequence encoded by a nucleic acid sequence represented as a whole or in part by a sequence represented by SEQ ID NO 1, an analogue thereof or a fragment thereof, of at least one nucleic sequence encoding such a polypeptide or of at least one agent modulating the activity or the expression of such a polypeptide as an agent useful for stimulating a terminal epithelial differentiation, and in particular of the epidermal type.

According to another of its aspects, the subject of the present invention is also a use of an effective quantity of at least one polypeptide derived from apolipoprotein D and, in particular, having an amino acid sequence encoded by a nucleic acid sequence represented as a whole or in part by a sequence represented by SEQ ID NO 1, an analogue thereof or a fragment thereof, of at least one nucleic sequence encoded by such a polypeptide or of at least one agent modulating the activity or the expression of such a polypeptide for the preparation of a composition, in particular a therapeutic composition, intended for stimulating an epithelial differentiation, and in particular terminal epidermal differentiation.

In particular, the compositions considered according to the invention may be intended for stimulating the terminal differentiation of the keratinocytes.

For the purposes of the present invention, the expression "effective quantity" is understood to mean the minimum quantity necessary to observe the expected effect, namely a cosmetic effect or a therapeutic effect, it being understood that the effective quantities necessary to obtain a cosmetic effect or a therapeutic effect may be, where appropriate, identical or different.

For the purposes of the invention, the expression "cosmetic use" is understood to mean a use intended mainly to provide an aesthetic effect and/or comfort.

For the purposes of the invention, the expression "therapeutic composition" is understood to mean a composition intended to provide a prophylactic or curative effect with regard to epithelial, and in particular epidermal, disorders recognized as being a manifestation of a pathological state.

The expression "prophylactic" or "preventive", for the purposes of the invention, is understood to mean the decrease in the risk of onset of a phenomenon, for example a pathology.

A composition in accordance with the invention may, in particular, be intended for preventing and/or treating a reduction in the thickness of an epithelium, in particular of an epidermis and/or a loss of firmness, elasticity, density and/or tone of an epithelium, in particular of an epidermis and/or the signs of skin ageing, such as the formation of wrinkles and fine lines.

The expression cutaneous signs of ageing is understood to mean any change in the external appearance of the skin due to ageing, whether it is chronobiological and/or photoinduced, such as for example wrinkles and fine lines, withered skin, lack of elasticity and/or of tone of the skin, reduction in the thickness of the dermis and/or degradation of collagen fibres, which causes the appearance of flabby and wrinkled skin. It is also understood to mean any internal changes in the skin which do not systematically result in a changed external appearance, such as for example any internal degradation of the skin, particularly of the elastin fibres, or of the elastic fibres, following exposure to ultraviolet radiation.

According to another embodiment, a composition in accordance with the invention may in particular be intended for preventing and/or treating the cutaneous signs of dryness, in particular for preventing and/or treating dehydration of an epithelium, in particular of an epidermis.

A composition in accordance with the invention may in particular be intended for preventing and/or treating the effects of the chronological ageing of an epithelium, in particular of an epidermis or of the lips or of the scalp.

According to another aspect, the present invention also relates to the use of at least one polypeptide in accordance with the invention as a tool for screening biological or chemical compounds capable of modulating, and in particular of activating, the expression and/or the biological activity of the said polypeptide.

In particular, it relates to a method of screening anti-ageing active agents comprising at least the steps consisting in:

a) bringing at least one cell type capable of expressing a polypeptide in accordance with the invention, that is to say apolipoprotein D or one of its derivatives, into contact with at least one chemical or biological compound to be tested, under conditions favourable for a manifestation of the expression of the said polypeptide, and b) determining the content of the said polypeptide.

According to yet another of its aspects, the present invention also relates to the use of at least one polypeptide in accordance with the invention, or of at least one nucleic acid sequence encoding the said polypeptide, as a tool for characterizing the state of an epithelium, and in particular of an epidermis.

More precisely, the present invention relates, according to another of its aspects, to a non-invasive method, in particular a cosmetic method, for characterizing the surface state of an epithelium, in particular of an epidermis, comprising at least the qualitative or quantitative characterization of the expression and/or of the biological activity of a polypeptide in accordance with the invention, that is to say apolipoprotein D, of one of its derivatives or fragments.

According to one variant embodiment, the data or value obtained may be assessed in comparison with a reference data item or value, obtained for example from at least an epithelium, in particular an epidermis, distinct from that which is the subject of the characterization, and whose state is known.

The aim of the present invention is also, according to another of its aspects, a non-invasive method, in particular a cosmetic method, for characterizing the efficacy of a cosmetic or therapeutic treatment aimed at improving the physiological state of an epithelium, in particular of an epidermis, and/or for treating a reduction in the thickness of an epithelium, in particular of an epidermis, and/or a loss of firmness, elasticity, density and/or tone of an epithelium, in particular of an epidermis, and/or the signs of skin ageing, such as wrinkles or fine lines comprising at least the qualitative or quantitative characterization of the expression and/or the biological activity of a polypeptide in accordance with the invention, that is to say of apolipoprotein D, of one of its derivatives or fragments.

According to one variant embodiment, the data obtained at the end of the characterization may also be examined in comparison with a reference value or data. This reference value or data may be data obtained from the epithelium, in particular the epidermis, to be subjected to the treatment, prior to the administration of the said treatment or within a shorter chronological time in relation to the treatment start date.

As is evident from the description which follows, the methods according to the invention are particularly advantageous since their use does not require an invasive operation.

The methods of the invention may be performed in vitro, ex vivo, or in vivo.

Indeed, the location, by the inventors of the novel ageing biomarker apolipoprotein D in the *stratum corneum* makes the quantitative or qualitative characterization of the expression of this glycoprotein possible by mere topical sample collection. The sample collection method may be for example a stripping-type technique consisting in applying to the epithelium considered, such as an epidermis, a portion of adhesive tape. On removing this adhesive tape, a fraction of the epithelium, for example an epidermal fraction, is removed. This is then, after extraction, analyzed by conventional methods such as immunoenzymatic assay or more particularly a Western-blot analysis.

Polypeptide Definition

According to one embodiment, a polypeptide suitable for the invention may have an amino acid sequence represented as a whole or in part by a sequence represented by SEQ ID NO 2, or an analogue thereof, or a fragment thereof.

For the purposes of the present invention, the expression ApoD is understood to mean, in general, unless otherwise stated, the sequence (SEQ ID NO 2) of the protein having or not having glycosylations on the asparagine residues nos. 45 and 178, leading to variants of molecular weight of 19 to 32 kDa and of pI 5.6 to 7.8.

The expression "analogue of a polypeptide" is understood to mean any polypeptide having a sequence homology, in particular towards one of the sequences characteristic of the said polypeptide, and a biological activity of the same nature.

This compound may be a peptidomimetic agent.

The homology may be at least 85%, for example at least 90%, and for example at least 95%. The homology may be determined by visual comparison or by means of any computer tool generally used in the field, such as the BLAST programmes available on www.ncbi.nlm.nih.gov and used with the default configured parameters.

The sequence homology may result from modifications derived from mutation or variation in the sequences of the peptides according to the invention resulting either from the deletion of one or more amino acids, or from the insertion of one or more amino acids, or else from the substitution of one or more amino acids in the sequences characteristic of a polypeptide according to the invention.

For the purposes of the invention, the expression "polypeptide fragment" is understood to mean any portion of a polypeptide in accordance with the invention comprising at least 4, at least 6, in particular at least 8, and more particularly at least 12 consecutive amino acids of the said polypeptide, and a substantially similar biological activity.

The expression "sequence characteristic of the polypeptide" is understood to mean in particular in relation to apolipoprotein D, the sequence represented by SEQ ID NO 2.

In general, the polypeptide analogues may comprise conservative substitutions in relation to the amino acid sequence of the natural polypeptide.

Several of these modifications may be combined.

By way of example of mutations which may be considered in the present invention, there may be mentioned, without being exhaustive, the replacement of one or more amino acid residues with amino acid residues having a similar hydropathic value without as a result substantially affecting the biological properties of the polypeptide, and in particular its biological activity such as its activity in stimulating the proliferation and/or migration and/or terminal differentiation of the keratinocytes or in stimulating the synthesis of proteoglycans in an epithelium, and in particular the epidermis.

The hydropathic value is a value attributed to amino acids according to their hydrophobicity and their charge (Kyte et al. (1982), J. Mol. Biol., 157: 105).

A polypeptide or analogue also covered by the present invention may be a polypeptide which has undergone one or more post-translational modifications.

The expression "post-translational modifications" is understood to include all the modifications which a peptide or a protein is liable to undergo at the end of its synthesis in a cell, such as for example one or more phosphorylations, one or more glycosylations, one or more lipidations, such as a farnesylation or a palmitoylation, a structural rearrangement such as formation of disulphide bridges and/or such as cleavage within the peptide sequence.

The analogue substantially exhibits, moreover, the same biological activity as the natural polypeptide.

According to one embodiment, a polypeptide suitable for carrying out the invention may also be a natural or synthetic polypeptide, where appropriate capable of being obtained by enzymatic or chemical lysis of apolipoprotein D or by chemical or biological synthesis or by extraction from a biological tissue, such as for example the skin, expressing this polypeptide naturally or after transfection, and the various post-translational forms thereof, or else any natural or synthetic polypeptide whose sequence totally or partially comprises (as a whole or in part) an abovementioned amino acid sequence, for example the variants and the analogues.

Persons skilled in the art may obtain a polypeptide in accordance with the invention by means of recombinant DNA-based methods, such as for example those described in the manual "Molecular Cloning—A Laboratory Manual" ($2^{nd}$ edition), Sambrook et al., 1989, Vol. I-III, Coldspring Harbor Laboratory, Coldspring Harbor Press, NY, (Sambrook).

According to another embodiment, a polypeptide suitable for carrying out the invention may also be a polypeptide as defined above in which at least one residue has been replaced by an amino acid residue with a similar hydropathic value, as defined above.

According to another embodiment, a polypeptide suitable for carrying out the invention may also be a polypeptide as defined above, fused with another polypeptide, a hydrophilic or hydrophobic targeting agent, a bioconversion precursor, a luminescent, radioactive or colorimetric marker.

Without being limiting, there may be mentioned, as example of compounds which may be coupled with a polypeptide in accordance with the invention, fluorescent proteins such as the "Green Fluorescent Protein", fluorescent chemical compounds such as rhodamine, fluorescein, Texas Red®, phosphorescent compounds, radioactive elements, such as 3H, $^{14}C$, $^{35}S$, $^{121}I$ or $^{125}I$, or colorimetric markers such as chromogenic substrates that are sensitive to the action of galactosidase, peroxidase, chloramphenicol acetyltransferase, luciferase or alkaline phosphatase.

Depending on the nature of the compounds capable of being coupled with a polypeptide in accordance with the invention, the coupling may be performed by chemical methods, in particular by means of reactive chemical functional groups or by molecular biology methods known to a person skilled in the art.

Definition of Nucleic Acid Sequences

According to one embodiment, the present invention also relates to nucleic acid sequences encoding a polypeptide of the invention and their use in the various uses and methods in accordance with the invention.

Accordingly, the present invention also relates to the use of nucleic acid, in particular deoxyribonucleic acid or ribonucleic acid, sequences encoding a polypeptide in accordance with the invention, in particular the sequences corresponding to at least one nucleic acid sequence represented by SEQ ID NO: 1, analogues thereof or a fragment thereof, for the preparation of a composition in accordance with the invention.

For the purposes of the present invention, the expression "fragment of a nucleic acid sequence" is understood to mean a nucleic acid sequence encoding all or part of a polypeptide in accordance with the invention, or an analogue thereof, and in particular a nucleic acid sequence represented by SEQ ID NO 1 or an analogue thereof.

The expression "analogue of a nucleic acid sequence" is understood to mean any nucleic acid sequence, optionally resulting from the degeneracy of the code for the nucleic acids, and encoding a sequence of a polypeptide identical or analogous to the polypeptide sequence encoded by the said nucleic acid sequence.

The nucleic acid sequences may be of any origin possible, namely either of animal, in particular mammalian and more preferably still human, origin, or of plant origin, or of microbial origin (viruses, phages, bacteria and the like) or else of fungal origin, without prejudice to whether they are present or not present naturally in the said organism of origin.

In this instance, the invention also relates to the use of isolated and purified nucleic acid fragments encoding the polypeptides considered according to the invention.

A nucleic acid sequence in accordance with the invention may comprise a sense, an anti-sense or an interfering sequence corresponding to a sequence encoding a polypeptide in accordance with the invention.

Accordingly, the present invention also relates to the use of nucleic acid, in particular deoxyribonucleic acid or ribonucleic acid, sequences encoding a polypeptide in accordance with the invention.

The nucleic acid sequences according to the invention may be used in particular to prepare corresponding sense or anti-sense ribonucleic acid sequences.

The subject of the invention is also the use of any polynucleotide, having a ribonucleic or deoxyribonucleic acid sequence, comprising a sense or anti-sense sequence, in particular "small interferent RNA", corresponding to at least the nucleic acid sequence SEQ ID NO: 1 or an analogue thereof.

Modulating Agent

According to another embodiment, the invention relates to the use of an agent modulating the expression, the activity and/or the release of a polypeptide in accordance with the invention.

In particular, the invention relates to the use of a modulating agent activating the activity of a polypeptide of the invention.

For the purposes of the invention, the expression "modulate" is understood to mean, in relation to a given effect, the action of stimulating or inhibiting this effect.

For the purposes of the present invention, the expression "modulating agent or chemical or biological compound capable of modulating biological activity and/or expression" is understood to mean any compound capable of acting, directly or indirectly, on at least one polypeptide in accordance with the invention, or a nucleic acid sequence encoding it, or on a component of an intra- or extracellular signalling pathway, or a metabolic pathway, involving the said polypeptide, or on a component involved in the regulation of transcription and/or the translation of a nucleic acid sequence encoding the said polypeptide.

The expression "biological activity" is understood to mean in particular in relation to apolipoprotein D the biological activity of the protein having the sequence represented by SEQ ID NO 2, of the mature form of the protein and the protein having or not having glycosylations on the asparagine residues Nos. 45 and 178 leading to variations in molecular weight from 19 to 32 kDa and in pI from 5.6 to 7.8.

This modulating agent may be an agent activating gene expression or protein expression or else an agent inhibiting gene expression or protein expression of a polypeptide of the invention.

By way of illustration, and without limitation, of agents activating gene expression, there may be mentioned in particular androgens (dihydrotestosterone (DHT)), dexamethasone (DEX), trans-retinoic acid, 1,25-dihydroxyvitamin D3, clozapine, alpha-interleukin 1 and glucocorticoids.

By way of illustration, and without limitation, of the agents inhibiting gene expression, there may be mentioned in particular baicalein, estrogens (estradiol) and tamoxifen.

More particularly, the modulating agent may be an activator of gene expression of the polypeptides according to the invention.

The present invention additionally relates to a method of screening biological or chemical compounds or physicochemical factors capable of modulating a biological activity of a polypeptide according to the invention comprising at least the steps consisting in:

a) bringing at least one polypeptide in accordance with the invention into contact with at least one chemical or biological compound to be tested and/or subjecting the said polypeptide to the said physicochemical factor, under conditions favourable for the manifestation of the said biological activity of the said polypeptide, and b) determining the said biological activity of the said polypeptide.

In such a method, the biological activity of the polypeptide, in particular its epithelial differentiation activity, and in particular terminal epidermal differentiation, in particular in relation to the keratinocytes, may for example be determined by any method known to a person skilled in the art.

For example, and without being limiting, there may be mentioned methods of cell culture followed by characterization of differentiation markers, such as for example keratin 10, filaggrin or proliferation markers such as for example KI 67 and PCNA.

According to one embodiment, the biological activity of the polypeptide may be compared to a reference value.

A reference value may be obtained by measuring the biological activity of the polypeptide in the absence of any biological or chemical compound or physicochemical factor to be tested.

Assuming that this measurement of a reference value is carried out before the use of the biological or chemical compound or physicochemical factor to be tested, the method according to the invention can additionally make it possible, where appropriate, to assess the potential efficacy of the said compound.

It is possible for this biological activity not to be affected by the presence of the said compound or on the other hand to be inhibited or stimulated.

Assuming that a stimulant effect is observed, the compound tested is capable of being used for example as an anti-ageing active agent.

A method in accordance with the invention may be carried out on an isolated cellular sample obtained either from a skin biopsy or from cultured cells.

Advantageously, a keratinocyte sample may be mentioned as cellular sample suitable for the invention.

Advantageously, a polypeptide used in the method according to the present invention may be apolipoprotein D.

The present invention also relates to a method of screening biological or chemical compounds capable of modulating the expression of a polypeptide in accordance with the invention, comprising at least the steps consisting in:

a) bringing at least one cellular type capable of expressing a nucleic acid sequence encoding the said polypeptide in accordance with the invention into contact with at least one chemical or biological compound to be tested, under conditions favourable for the manifestation of the expression of the said sequence, and b) determining the expression of the said nucleic acid sequence.

The expression of a nucleic acid sequence may be determined, for example, by means of oligonucleotide probes, or by any protocol known to a person skilled in the art.

By way of example of methods of detecting a nucleic acid sequence, mention may be made of the polymerase chain reaction (PCR), the reverse transcriptase polymerase chain reaction (RT-PCR or Q-PCR), Northern blotting, ribonuclease protection assay method, methods with DNA chips, methods with transcriptomic chips, methods with oligonucleotide chips, in situ hybridization methods.

By way of example of agents suitable for the detection of a nucleic acid sequence, and in particular of an mRNA sequence, there may be mentioned a labelled nucleic acid probe which can hybridize with the said sequence.

Such a nucleic acid probe can be easily obtained by any method known to a person skilled in the art.

Accordingly, the nucleic acid sequences in accordance with the invention may be used to produce sense and/or antisense oligonucleotide primers, which hybridize, under high-stringency conditions, with the sequence SEQ ID NO: 1 or an analogue thereof.

The expression of a nucleic acid sequence in accordance with the invention may be compared to a reference value obtained, for example, by carrying out a method in accordance with the invention in the absence of a test compound.

The expression of a nucleic acid sequence can also be determined, indirectly, by the determination of the expression of the polypeptide encoded by the said sequence, by means of any technique known in the field, such as Western blotting, ELISA, the Bradford or Lowry method, or as indicated below.

The present invention also relates to a method of screening biological or chemical compounds, or even anti-ageing active agents, capable of modulating the expression of a polypeptide in accordance with the invention, comprising at least the steps consisting in:

a) bringing at least one cellular type capable of expressing a polypeptide in accordance with the invention into contact with at least one chemical or biological compound to be tested, under conditions favourable to the manifestation of the expression of the said polypeptide, b) determining the polypeptide content, and c) comparing the said content determined in step b) to a content of the said polypeptide determined in the absence of chemical or biological compound to be tested.

The comparison performed in step c) may make it possible to deduce information regarding the property of the said test compound to modulate the expression of a polypeptide in accordance with the invention.

A method of the invention may be performed on an isolated cellular sample.

The determination of a polypeptide content in accordance with the invention may be performed by means of any method known to persons skilled in the art.

As methods for the detection of a polypeptide, there may be mentioned Western blotting, slot blotting, dot blotting, ELISA (Enzyme Linked Immuno-Sorbent Assay) methods of the singleplex or multiplex type, proteomic or glycomic methods, methods of staining polypeptides in a polyacrylamide gel with a silver-based stain, with Coomassie blue or with SYPRO, immunofluorescence methods, UV absorption methods, conventional, electron or confocal microscopy immunohistochemical methods, FRET (fluorescence resonance energy transfer) methods, TR-FRET (time-resolved FRET) methods, FLIM (fluorescence lifetime imaging microscopy) methods, FSPIM (fluorescence spectral imaging microscopy) methods, FRAP (fluorescence recovery after photobleaching) methods, reporter gene methods, AFM (atomic force microscopy) methods, surface plasmon resonance methods, microcalorimetry methods, flow cytometry methods, biosensor methods, radioimmunoassay (RIA) methods, isoelectric focusing methods, enzymatic tests, methods using peptide chips, sugar chips, antibody chips, mass spectrometry methods, SELDI-TOF type spectrometry methods (Ciphergen).

The methods in accordance with the invention may be carried out on a sample, for example isolated from the epithelium, in particular the epidermis, obtained from a skin biopsy or an epithelial, for example epidermal, cellular model or more advantageously from a non-invasive surface removal, in particular with an adhesive tape ("stripping tape"), of *stratum corneum* or by simple washing.

An epidermis sample can be collected by any method known to persons skilled in the art.

These methods may be carried out by so-called stripping techniques.

These strippings are sticky surfaces applied to the surface of the epidermis such as Blenderm® from 3M, D'squam (commercial adhesive from CuDERM), cyanoacrylate glue or the varnish stripping method. Using these strippings, the adherent corneocytes and the contents of their intercellular spaces may be collected and subsequently subjected to an extraction which makes it possible to access the protein content.

The collection of a sample suitable for the method may also be performed more directly by "washing" of the skin surface by means, for example, of accessories of the vane turbine type, of the spiral cell type (as described in patent FR 2 667 778) combined with a fluid circuit, or simply by addition/removal of a drop of buffer at the surface of the skin.

As a guide for other sample collection methods appropriate for carrying out the invention, there may be mentioned methods based on scraping the top part of the *stratum corneum* by means of a twin blade system. This technique makes it possible to collect squamae which can then be directly analysed by various techniques in order to determine the mineral, amino acid or lipid levels.

It is understood that all the cosmetic or therapeutic compositions considered according to the invention use a physiologically acceptable medium.

For the purposes of the present invention, the expression "physiologically acceptable medium" is understood to mean a medium suitable for the application of a composition to an epithelium or a keratin material, such as the skin, the scalp, the lips, the mucous membranes and keratin fibres such as the hair, the nails and body hairs, or where appropriate by the oral or parenteral route.

For the purposes of the present invention, the expression "therapeutic" is understood to mean a composition which can be used in the context of a prophylactic and/or curative treatment, or of a method for evaluating the state of an epithelium, and in particular of the epidermis.

According to another embodiment, a cosmetic or therapeutic composition in accordance with the invention may additionally comprise at least one cosmetic and/or therapeutic active agent.

As examples of active agents which can be used in the context of the present invention, mention may be made of cosmetic oils, such as silicone oils or vegetable oils of the triglyceride type, hydrocarbon oils such as parleam oil and esters of fatty acids and of fatty alcohols.

It may also be possible to use other active agents which make it possible to improve the condition of the skin, such as hydrating or moisturizing active agents or active agents which make it possible to improve the natural lipid barrier, such as ceramides, cholesterol sulphates and/or fatty acids and mixtures thereof.

It may also be possible to use enzymes having activity on the skin, such as proteases, lipases, glucosidases, amidases, cerebrosidases and/or melanases and mixtures thereof.

As other examples of active agents suitable for carrying out the present invention, there may be mentioned: analgesic active agents, anti-yeast active agents, antibacterial active agents, antiparasitic active agents, antifungal active agents, antiviral active agents, steroidal anti-inflammatory active agents, anaesthetic active agents, antipruritic active agents, keratolytic active agents, anti-free radical active agents, antiseborrheic active agents, antidandruff active agents, anti-acne active agents, active agents intended for preventing ageing of the skin and/or for improving its condition, anti-dermatitis active agents, antiirritant active agents, immunomodulatory active agents, active agents for the treatment of dry skin, antiperspirant active agents, antipsoriatic active agents, active agents for protecting against UV, antihistamine active agents, wound-healing active agents, self-tanning active agents, antioxidants such as green tea or active fractions thereof, glycerine, laponite, caffeine, aromatic essential oils, colorants, depigmenting active agents, liporegulators, emollients, refreshing, deodorizing, desensitizing, bleaching and nourishing active agents, agents reducing skin differentiation and/or proliferation and/or pigmentation, and mixtures thereof.

In general, any composition of the invention may be applied to the skin (on any skin region of the body) or on the mucous membranes (buccal, jugal, gingival, genital and conjunctival mucous membranes, and the like).

In a known manner, a cosmetic composition may also contain adjuvants customarily used in the cosmetic field, such as hydrophilic or lipophilic gelling agents, hydrophilic or lipophilic additives, preservatives, antioxidants, solvents, perfumes, fillers, screening agents, odour absorbers and colouring materials.

The quantities of the various constituents of the compositions according to the invention are those conventionally used in the fields considered.

The quantity of chemical or biological compound or of polypeptide, nucleic acid sequence or modulating agent in accordance with the invention contained in a composition according to the invention, also termed "effective quantity", of course depends on the nature of the compound and the desired effect and may therefore vary widely.

To give an order of magnitude, a composition may contain a modulating agent in accordance with the invention or a polypeptide in a quantity representing from 0.00001% to 50% of the total weight of the composition, in particular in a quantity representing from 0.001% to 10% of the total weight of the composition, and more particularly in a quantity representing from 0.1% to 1% of the total weight of the composition.

A composition according to the invention may be more particularly designed for reducing and/or treating conditions liable to cause deterioration of the state of an epithelium, in particular of an epidermis.

A state of an epithelium covered by the present invention may be a state linked to a dysfunction in terminal epithelial, in particular epidermal, differentiation, in particular of the keratinocytes.

Such a state may be of chronological origin (i.e. linked to the time elapsed such as skin ageing) and/or a sign of a skin disorder, linked for example to photoageing.

Accordingly, a composition in accordance with the invention, in particular a cosmetic composition, may in particular be intended for preventing and/or treating a reduction in the thickness of an epidermis and/or a loss of firmness, elasticity, density and/or tone of an epidermis and/or the formation of wrinkles and fine lines.

According to another embodiment, a composition in accordance with the invention, in particular a cosmetic composition, may in particular be intended for preventing and/or treating the cutaneous signs of dryness, in particular for preventing and/or treating dehydration of an epidermis.

A composition of the invention may also be intended for preventing and/or treating disorders of the barrier function of an epithelium, in particular of an epidermis.

According to another embodiment, a composition in accordance with the invention, in particular a cosmetic composition, may be intended for preventing and/or treating the signs of epidermal ageing.

A composition in accordance with the present invention, in particular a therapeutic composition, may be more particularly intended for the treatment of a skin disorder such as a skin hydration disorder such as xerosis, parakeratosis, hyperkeratosis, ichtyosis, psoriasis, atopic dermatitis, eczema, rosacea, lichen, pruritus, a skin pathology having an inflammatory component or resulting from an impairment of the immune response, desquamation, disruption of melanogenesis or of sebogenesis, alopecia, hirsutism, a wound-healing disorder, or a skin disorder involving secretion phenomena and cellular invasion processes, in particular in the context of malignant or benign neoplasias.

According to another aspect, the present invention also relates to the use of at least one polypeptide in accordance with the invention or of at least one nucleic acid sequence encoding the said polypeptide, as a tool for characterizing the state of an epithelium, and in particular of an epidermis.

By way of example, it is possible to characterize according to the invention the state of an epithelium chosen from desquamation, ichtyosis, hyperkeratosis, dryness of an epidermis, ageing or photoageing.

Accordingly, as specified above, the present invention relates, according to another of its aspects, to non-invasive methods for characterizing the surface state of a non-pathological epidermis or the efficacy of a cosmetic or therapeutic treatment intended for qualitatively or quantitatively characterizing the expression of apolipoprotein D, of one of its derivatives or fragments.

These methods are particularly advantageous since their use does not require necessarily resorting to an operating technique for carrying out such a characterization. An epidermis extract may thus be obtained by simple stripping and directly analyzed by a conventional analytical technique, in particular as described above.

According to one embodiment, a method for characterizing the state of an epithelium, for example an epidermis, comprises at least the steps consisting in:

a) determining, in a sample of the said epithelium, the content of polypeptide in accordance with the invention, or of a nucleic acid sequence encoding the said polypeptide, and b) comparing the said content determined in step a) to a reference value.

Advantageously, a method of the invention is non-invasive.

A method of the invention is advantageously carried out on an isolated sample.

According to one embodiment, a method according to the invention may be carried out on a sample of epithelium, in particular of epidermis, collected from an individual.

A method according to the invention may also be carried out on a sample of epithelium, and in particular of epidermis, collected from an epithelial, and in particular epidermal, cellular model, or from an isolated skin reconstructed so as to qualify the state thereof.

An epithelium sample may be collected by any method known to persons skilled in the art.

A method according to the invention may be carried out in vivo, in vitro or ex vivo.

A reference value may be, for example, a content of polypeptide or of nucleic acid sequence determined on an epidermis sample collected from an epithelium, and in particular a normal skin, that is to say that is satisfactory from a physiological point of view, just like for example a young skin.

A reference value may be measured in parallel with or following the determination of the said content of a polypeptide or of a nucleic acid sequence.

A comparison of a determined content with a reference value may make it possible to evaluate a deviation relative to this value.

Analysis of the intensity and/or of the nature of this deviation (negative or positive) may be informative for the state of the epidermis.

The characterization of the state of an epidermis may be a sign of a potential skin disorder which may be corrected by the use of compounds capable of modulating the expression of a polypeptide according to the invention.

According to one embodiment, a method according to the invention may be carried out in a method for the in vivo, in vitro or ex vivo diagnosis of a presumed disorder of an epithelium, in particular of the epidermis, in an individual.

For example, the state of an epithelium to be evaluated may be chosen from desquamation, ichtyosis, hyperkeratosis, dryness of an epidermis, ageing or photoageing.

A polypeptide suitable for carrying out a method according to the invention may be advantageously apolipoprotein D.

The determination of the content of polypeptide in accordance with the invention or of nucleic acids in accordance with the invention in an epidermis sample may be carried out by any protocol known to persons skilled in the art.

As methods for detecting a polypeptide, mention may be made of those cited above.

Accordingly, it is possible to envisage detecting the presence of a polypeptide in accordance with the invention by means of an antibody, where appropriate in a labelled form.

An antibody capable of being used as a tool for evaluating the state of an epidermis may be obtained by any method known to persons skilled in the art, as described in "Antibodies: A Laboratory Manual", Cold Spring Harbor Laboratory Press, Cold Spring Harbor, N.Y. (1990). Advantageously, the antibodies used may be recombinant antibodies such as those developed by the company Antibodies-by-design.

A nucleic acid sequence suitable for carrying out a method according to the invention may be advantageously a nucleic acid sequence encoding ApoD, for example of the mRNA type.

By way of example of methods for detecting nucleic acids in accordance with the invention, mention may be made of the methods cited above.

The present invention also relates to a nontherapeutic method for demonstrating the effect of a treatment liable to cause regression of a disorder of an epithelium, in particular a skin or scalp disorder, in an individual, comprising at least the steps consisting in:

a) carrying out, before the treatment, at least a first determination, in a first sample of an epithelium collected from the said individual, of a biological activity and/or of the expression of a polypeptide in accordance with the invention, or of the expression of a nucleic acid sequence encoding the said polypeptide, b) carrying out, after the treatment, at least a second determination, in a second sample of an epithelium collected from the said individual, of the said biological activity and/or of the said expression of the said polypeptide or of the said expression of the said nucleic acid sequence determined in step a), and c) comparing the first and second determinations, in particular in order to deduce therefrom information relating to the effect at least of the treatment.

Such a treatment may in particular be a cosmetic treatment.

In particular, the treatment whose effect is to be evaluated may be a treatment intended for relieving or reducing a skin or scalp disorder linked to a keratinocyte proliferation and/or differentiation dysfunction.

The biological activity and the expression of a polypeptide may be determined as indicated above.

According to another aspect, the present invention relates to a method for the cosmetic treatment of a skin disorder comprising at least one step consisting in applying at least one cosmetic composition in accordance with the invention to at least part of the skin, mucous membranes and/or keratin fibres.

According to another aspect, the present invention relates to the use of an effective quantity of at least one polypeptide in accordance with the invention or of at least one agent modulating the expression of the said polypeptide for preparing and/or improving a pluristratified cellular model, in particular of the epidermal or mucous membrane type, and in particular a model of reconstructed skin.

For the purposes of the invention, the expression "model of reconstructed skin" is understood to mean a model in which various cell types are combined, such as in particular the natural constituents of the skin, just like for example keratinocytes, fibroblasts, Langerhans' cells and melanocytes.

The cells of the fibroblast type may be irradiated or otherwise.

Such models and their preparation are known to persons skilled in the art.

For the purposes of the present invention, "a" should be understood in the sense of "at least one".

The examples presented below are presented by way of illustration and do not limit the invention.

EXAMPLE I

Analysis of Samples Collected by Varnish Stripping on Various Skin Regions of an Individual The analyses are carried out using varnish strippings performed on the legs.

The subjects suitable for the study are put into 4 groups.

The AS group corresponds to group 1: dry menopausal individuals n=15.

The AN group corresponds to group 2: normal menopausal individuals n=13.

The JS group corresponds to group 3: dry young individuals n=16.

The JN group corresponds to group 4: normal young individuals n=14.

1: Preparation of Acetone Powders

Two varnish strippings (B. Mehul et al., J Biol Chem 2000, Apr. 28; 275(17): 12841-7) of 10 cm$^2$ are placed in 20 ml of acetone. The corneocytes become detached. The mixture is filtered on a 40 µm nylon membrane. Three successive rinses are performed with the same volume of acetone. The suspension is finally filtered on a vacuum pump. Acetone powders of *stratum corneum* are obtained in dry form.

2: Extraction of the Samples

An extraction is carried out under denaturing conditions. To do this, a prewash is performed with a volume (100 µl) of PBS buffer (Phosphate Buffer Saline)+0.1% Triton X100 is added per mg of acetone powder. The mixture is ground in a Potter and centrifuged. The corneocyte pellet is recovered. It is extracted with the same volume (100 µl/mg) of Laemmli buffer containing 0.0625 mM Tris pH 6.8, 200 mM DTT, 2% SDS, 10% glycerol. The mixture is heated at boiling temperature for 10 minutes, and then ground and centrifuged for 10 minutes at 10 000 g. The supernatant is recovered. An assay of proteins is performed according to the Bradford technique with the Bradford reagent (Bio-Rad Protein assay). The samples are adjusted to 1 mg/ml.

3: Analyses of the Proteins by Western Blotting

The proteins are separated by SDS-PAGE electrophoresis. After transferring semidry onto PVDF membrane (Immobilon-P Milipore) according to a standard protocol, the proteins are incubated with the anti-apolipoprotein D antibody Medcla 457 (36c6) (Accurate Chemical) overnight at 4° C. Next, the second incubation is performed with the secondary antibody, in this instance a mouse antibody (Goat anti-mouse IgG HRP conjugate) (Bio-Rad) directed against the first antibody for 1 h 30 min at room temperature. The total proteins present on the membranes after transfer are stained with amido black, after immunodetection. The ECL Plus kit (Amersham) is used for the visualization. The image is acquired with FluorSmax (Biorad) and the bands are quantified with the aid of the Quantity-one software (Biorad).

4: Results

The results are expressed as delta cnt*mm$^2$ of the protein of interest/delta cnt*mm$^2$ of the total proteins.

Methodology:

2-way analysis of variance in Age and Type of skin taking into account the interaction of these two factors+1-way analysis of variance (group) and Turkey's multiple comparison test. As the normality and homoscedasticity conditions were not verified, the analysis was performed after logarithmic transformation.

The statistical analysis was performed with the software packages SAS version 8.2 and SPSS version 12.

All the tests were performed at the 5% two-sided threshold.

The table below presents the mean results and their standard errors of the mean (sem).

| group | Apolipoprotein D | sem apoD |
|---|---|---|
| AS | 192 | 62 |
| AN | 206 | 76 |
| JS | 738 | 245 |
| JN | 728 | 201 |

A significant reduction is noted in the expression of apolipoprotein D during skin ageing (p=0.005).

The invention claimed is:

1. A method for characterizing the state of an epithelium comprising at least steps consisting in:
   a) determining in a sample of the epithelium a content of a polypeptide having the amino acid sequence of SEQ ID NO:2, and
   b) comparing the content determined in step a) to a reference value which is the content of the polypeptide obtained from an epithelium sample of a normal skin, the state of the epithelium being ageing, the state being characterized by a decrease between the reference value and the content determined in step a).

2. The method according to claim 1, wherein the method is non-invasive.

* * * * *